United States Patent
Asirvatham et al.

(10) Patent No.: US 11,897,834 B2
(45) Date of Patent: *Feb. 13, 2024

(54) BRANCHED AMINO ACID SURFACTANTS

(71) Applicant: AdvanSix Resins & Chemicals LLC, Parsippany, NJ (US)

(72) Inventors: Edward Asirvatham, Chatham, NJ (US); Andrei Honciuc, Iasi (RO); Voichita Mihali, Basel (CH)

(73) Assignee: AdvanSix Resins & Chemicals LLC, Parsippany, NJ (US)

( * ) Notice: Subject to any disclaimer, the term of this patent is extended or adjusted under 35 U.S.C. 154(b) by 11 days.

This patent is subject to a terminal disclaimer.

(21) Appl. No.: 17/365,770

(22) Filed: Jul. 1, 2021

(65) Prior Publication Data

US 2022/0009881 A1    Jan. 13, 2022

Related U.S. Application Data

(60) Provisional application No. 63/049,726, filed on Jul. 9, 2020.

(51) Int. Cl.
*C07C 309/22*   (2006.01)
*C07C 229/08*   (2006.01)
*C07C 229/12*   (2006.01)
*C09K 23/00*    (2022.01)

(52) U.S. Cl.
CPC .......... *C07C 309/22* (2013.01); *C07C 229/08* (2013.01); *C07C 229/12* (2013.01); *C09K 23/00* (2022.01)

(58) Field of Classification Search
CPC ... C07C 309/22; C07C 229/08; C07C 229/12; C07C 291/04; C07C 309/14; C07C 309/30; C09K 23/00; C11D 1/46; C11D 1/75; C11D 1/92
USPC ........................................................ 562/105
See application file for complete search history.

(56) References Cited

U.S. PATENT DOCUMENTS

| | | | |
|---|---|---|---|
| 4,194,052 | A | 3/1980 | Lewis et al. |
| 4,550,137 | A | 10/1985 | Dowbenko et al. |
| 5,851,982 | A | 12/1998 | Sakata et al. |
| 6,372,703 | B1 | 4/2002 | Richter et al. |
| 9,481,695 | B2 | 11/2016 | Knott et al. |
| 10,227,548 | B2 | 3/2019 | Zhang et al. |
| 2003/0060390 | A1 | 3/2003 | Demeyere et al. |
| 2007/0167347 | A1 | 7/2007 | Gallotti et al. |
| 2007/0179080 | A1 | 8/2007 | Gallotti et al. |
| 2008/0280865 | A1 | 11/2008 | Tobita |
| 2014/0246041 | A1 | 9/2014 | Krueger |
| 2015/0141315 | A1 | 5/2015 | Jin |
| 2016/0340610 | A1 | 11/2016 | Zhang et al. |
| 2017/0137750 | A1 | 5/2017 | Zhang et al. |
| 2017/0342346 | A1 | 11/2017 | Zhang et al. |
| 2017/0349859 | A1 | 12/2017 | Zhang et al. |
| 2018/0002639 | A1 | 1/2018 | Zhang et al. |
| 2018/0371366 | A1 | 12/2018 | Zhang et al. |
| 2019/0300822 | A1 | 10/2019 | Zhang et al. |

FOREIGN PATENT DOCUMENTS

| | | |
|---|---|---|
| CA | 2006439 A1 | 7/1990 |
| CN | 109154029 A | 1/2019 |
| DE | 10021538 B4 | 6/2008 |
| DE | 102015223826 A1 | 9/2016 |
| EP | 0385562 A2 | 9/1990 |
| EP | 0883600 B1 | 10/2001 |
| EP | 1584674 A | 10/2005 |
| EP | 3158042 B1 | 12/2018 |
| GB | 2310659 A | 9/1997 |
| JP | 01-190798 A | 7/1989 |
| JP | 08-232168 A | 9/1996 |
| JP | 08231478 * | 9/1996 |
| JP | 09-105076 A | 4/1997 |
| JP | 2001-048851 A | 2/2001 |
| JP | 3425227 B2 | 7/2003 |
| JP | 3502679 B2 | 3/2004 |
| JP | 3502680 B2 | 3/2004 |
| JP | 3563473 B2 | 9/2004 |
| JP | 2005-054327 A | 3/2005 |
| JP | 4156467 B2 | 9/2008 |
| JP | 2012-116755 A | 6/2012 |
| JP | 2014-129269 A | 7/2014 |
| WO | 96/03370 A1 | 2/1996 |
| WO | 97/31889 A1 | 9/1997 |
| WO | 2008/083967 A2 | 7/2008 |
| WO | 2017/101798 A1 | 6/2017 |
| WO | 2017/202289 A1 | 11/2017 |
| WO | 2018/077578 A1 | 5/2018 |
| WO | 2018/107410 A1 | 6/2018 |
| WO | 2018/200943 A1 | 11/2018 |
| WO | 2019/036030 A1 | 2/2019 |
| WO | 2019/110371 A1 | 6/2019 |

OTHER PUBLICATIONS

Machine translation JP 08231478, year 1996.*
International Search Report and Written Opinion received for PCT Patent Application No. PCT/US2021/040162, dated Oct. 18, 2021, 13 pages.
Anonymous, "Biocidal Compositions containing 4,4'-dichloro-2-hydroxydiphenylether (DCPP)," IP.com No. IPCOM000213522D, Dec. 20, 2011, pp. 1-36.
International Preliminary Report on Patentability received for PCT Patent Application No. PCT/US2021/040162, dated Jan. 19, 2023, 8 pages.

* cited by examiner

*Primary Examiner* — Ana Z Muresan
(74) *Attorney, Agent, or Firm* — Faegre Drinker Biddle & Reath LLP

(57) ABSTRACT

The present disclosure provides derivatives of amino acids that have branched alkyl structures and surface-active properties. The amino acid can be naturally-occurring or synthetic, or they may be obtained via a ring-opening reaction of a lactam, such as caprolactam. The amino acid may be functionalized to form a compound that is surface-active and have advantageous surfactant characteristics. The compounds of the present disclosure have low critical micelle concentrations (CMC) as well as superior ability to lower the surface tension of a liquid.

19 Claims, 10 Drawing Sheets

BRANCHED AMINO ACID SURFACTANTS

CROSS-REFERENCE TO RELATED APPLICATION

This application claims priority to U.S. Provisional Application No. 63/049,726, filed Jul. 9, 2020, which is herein incorporated by reference in its entirety.

FIELD

The present disclosure pertains to derivatives of amino acids and methods for their synthesis, wherein the amino acid derivatives include branched alkyl structures and have surface-active properties.

BACKGROUND

Surfactants (molecules with surface-active properties) are an important class of molecules with highly sought-after characteristics. Surfactants may be uncharged, zwitterionic, cationic, or anionic. Often, these compounds are amphiphilic molecules with a water-insoluble hydrophobic "tail" group and a water-soluble hydrophilic "head" group. These compounds may adsorb at an interface, such as an interface between two liquids, a liquid and a gas, or a liquid and a solid. In the case of an interface between water and oil, the hydrophilic head group extends into the water, while the hydrophobic tail extends into the oil. When added to water, the hydrophilic head group extends into the water, while the hydrophobic tail extends into the air. The presence of the surfactant disrupts the intermolecular interaction between water molecules, replacing it with weaker interactions between water molecules and the surfactant. This results in lowered surface tension and can also serve to stabilize the interface.

At sufficiently high concentrations, surfactants may form aggregates to limit the exposure of the hydrophobic tail to the polar solvent. One such aggregate is a micelle, in which the molecules are arranged in a sphere with the hydrophobic tails inside the sphere and the hydrophilic heads on the outside to interact with a polar solvent. The effect that a given compound has on surface tension and the concentration at which it forms micelles may serve as defining characteristics for a surfactant.

Surfactants are widely used in commercial applications in formulations ranging from detergents to hair care products to cosmetics. Compounds with surface-active properties are used as soaps, detergents, lubricants, wetting agents, foaming agents, and spreading agents, among others. Thus, there is an ongoing need to identify and synthesize such compounds.

However, solely from its structure, it may be difficult to predict whether a given compound would have surface-active properties, let alone other important characteristics such as interfacial adsorption dynamics, minimum surface tension achievable, and/or ability to wet hydrophobic and/or oleophobic surfaces, which are also integral to whether the compound would become a useful surfactant. Certain amino acids and their derivatives, for example, are desirable as building blocks for surfactants, but the selection of which amino acids to use is far from intuitive. Synthesis of such compounds adds another layer of difficulty due to the differences of solubilities attributable to different elements and moieties present in the same molecules. There remains a need for high-efficacy surfactants that can be readily synthesized at commercial scale via straightforward routes.

SUMMARY

The present disclosure provides derivatives of amino acids that have a branched alkyl structure, and which exhibit surface-active properties. The amino acids may be naturally occurring or synthetic amino acids, or they may be obtained via ring-opening reactions of molecules such as lactams, for example caprolactam. The amino acids may be functionalized to form compounds with surface-active properties. Characteristically, these compounds may have low critical micelle concentrations (CMC) and/or the ability to reduce the surface tension of a liquid.

The present disclosure provides compounds of Formula I, below, also referred to herein as the surfactant:

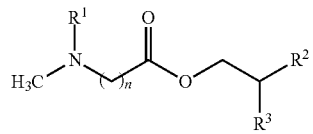

Formula I wherein $R^1$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); $R^2$ is $C_5$-$C_{12}$ alkyl; $R^3$ is $C_3$-$C_{10}$ alkyl; the terminal nitrogen is optionally further substituted with $R^4$, wherein $R^4$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide, iodide, and 4-methylbenzenesulfonate.

The present disclosure further provides compounds of Formula II, below, also herein referred to as the surfactant:

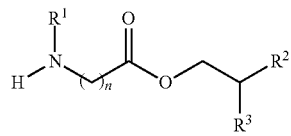

Formula II wherein $R^1$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); $R^2$ is $C_5$-$C_{12}$ alkyl; $R^3$ is $C_3$-$C_{10}$ alkyl; the terminal nitrogen is optionally further substituted with $R^4$, wherein $R^4$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide and iodide.

One specific compound provided by the present disclosure is 6-((2-butyloctyl)oxy)-N,N,N-trimethyl-6-oxohexan-1-aminium iodide, having the following formula:

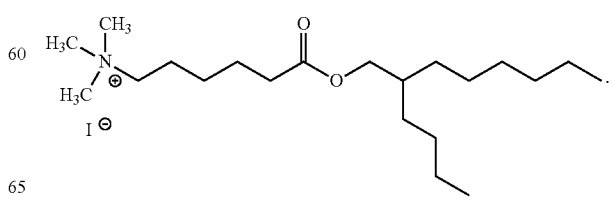

A second specific compound provided by the present disclosure is 6-((2-butyloctyl)oxy)-N,N-dimethyl-6-oxo-hexan-1-aminium 4-methylbenzenesulfonate, having the following formula:

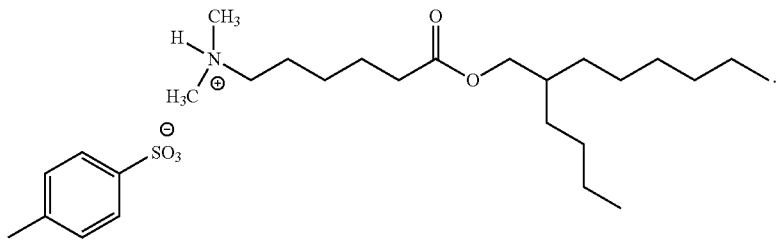

A third specific compound provided by the present disclosure is 6-((2-butyloctyl)oxy)-N,N-dimethyl-6-oxohexan-1-aminium chloride, having the following formula:

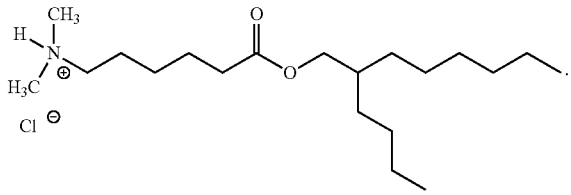 [SMILES: CCCCCCC(CCCC)COC(=O)CCCCC[NH+](C)C ; [Cl-]]

A fourth specific compound provided by the present disclosure is 4-((6-((2-butyloctyl)oxy)-6-oxohexyl)dimethylammonio)butane-1-sulfonate, having the following formula:

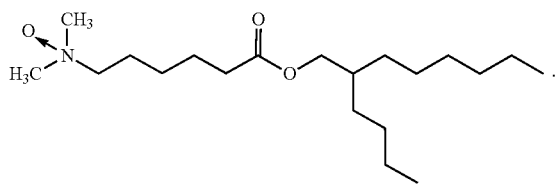

A fifth specific compound provided by the present disclosure is 2-butyloctyl 6-(dimethylamino)hexanoate N-oxide, having the following formula:

A sixth specific compound provided by the present disclosure is 6-((2-butyloctyl)oxy)-6-oxohexan-1-aminium chloride, having the following formula:

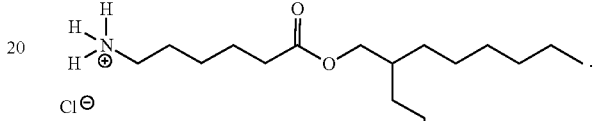

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
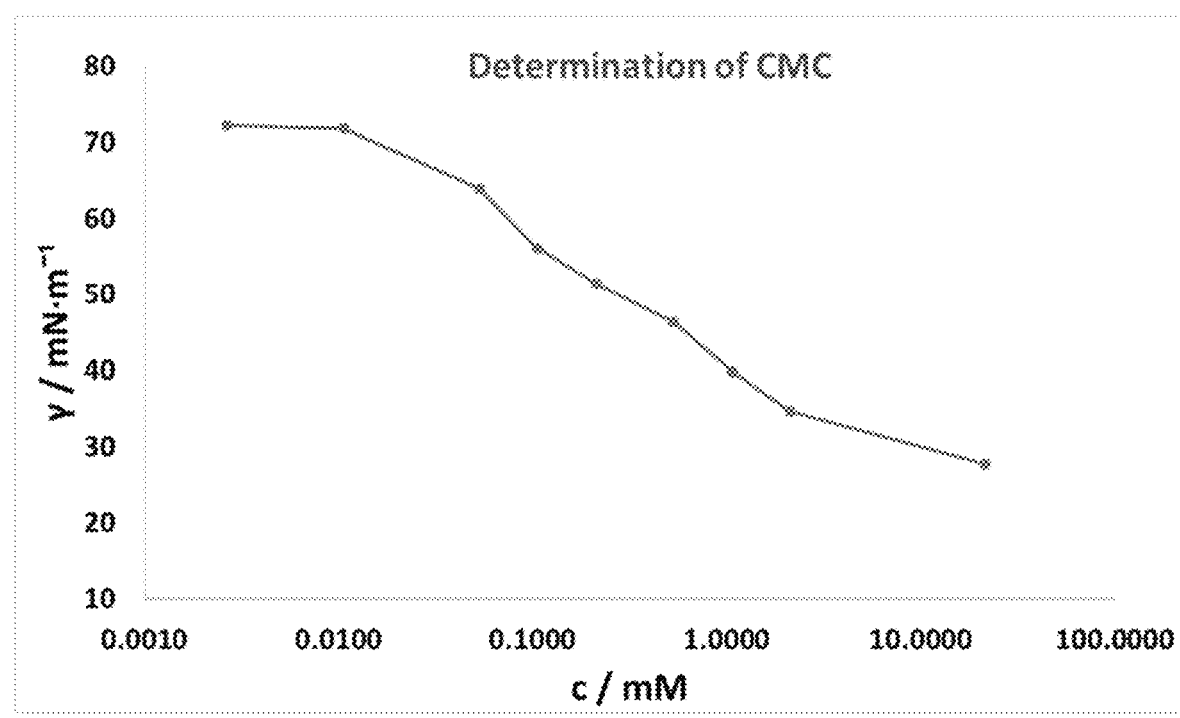
FIG. 1 shows a plot of surface tension versus concentration measured at pH=7 as described in Example 1B, wherein the Y axis depicts the surface tension (γ) in millinewtons per meter (mN/m) and the X axis depicts the concentration (c) in millimoles (mM).

I. Definitions.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the word "alkyl" means any saturated carbon chain, which may be a straight or branched chain.

As used herein, the phrase "surface-active" means that the associated compound is able to lower the surface tension of the medium in which it is dissolved, and/or the interfacial tension with other phases, and, accordingly, may be adsorbed at the liquid/vapor and/or other interfaces. The term "surfactant" may be applied to such a compound.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

II. Surfactant formulas.

The present disclosure provides derivatives of amino acids having a branched alkyl structure. The amino acids may be naturally occurring or synthetic, or they may be obtained from ring-opening reactions of lactams, such as caprolactam.

The compounds of the present disclosure have been shown to have surface-active properties, and may be used as surfactants and wetting agents, for example. In particular, the present disclosure provides compounds of Formula I, shown below:

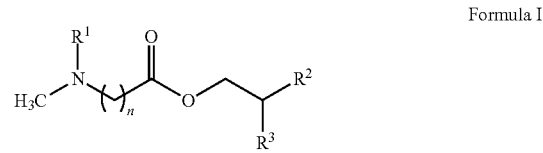

Formula I wherein $R^1$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); $R^2$ is $C_5$-$C_{12}$ alkyl; $R^3$ is C3-C10 alkyl; the terminal nitrogen is optionally further substituted with $R^4$, wherein $R^4$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide, iodide, and 4-methylbenzenesulfonate.

The present disclosure further provides compounds of Formula II, below, also herein referred to as the surfactant:

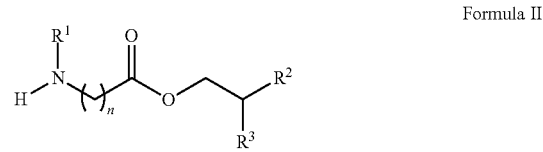

Formula II wherein $R^1$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); $R^2$ is $C_5$-$C_{12}$ alkyl; $R^3$ is $C_3$-$C_{10}$ alkyl; the terminal nitrogen is optionally further substituted with $R^4$, wherein $R^4$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide and iodide.

One specific compound provided by the present disclosure is 6-((2-butyloctyl)oxy)-N,N,N-trimethyl-6-oxohexan-1-aminium iodide, having the following formula:

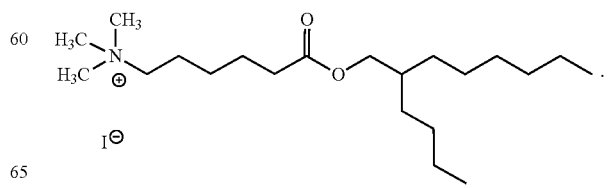

A second specific compound provided by the present disclosure is 6-((2-butyloctyl)oxy)-N,N-dimethyl-6-oxo-hexan-1-aminium 4-methylbenzenesulfonate, having the following formula:

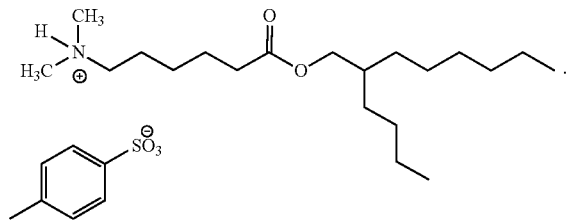

A third specific compound provided by the present disclosure is 6-((2-butyloctyl)oxy)-N,N-dimethyl-6-oxohexan-1-aminium chloride, having the following formula:

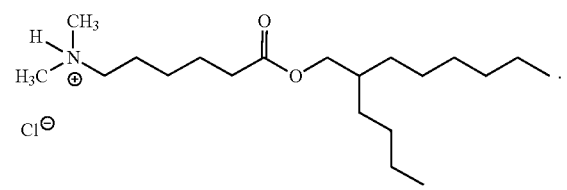

A fourth specific compound provided by the present disclosure is 4-((6-((2-butyloctyl)oxy)-6-oxohexyl)dimethylammonio)butane-1-sulfonate, having the following formula:

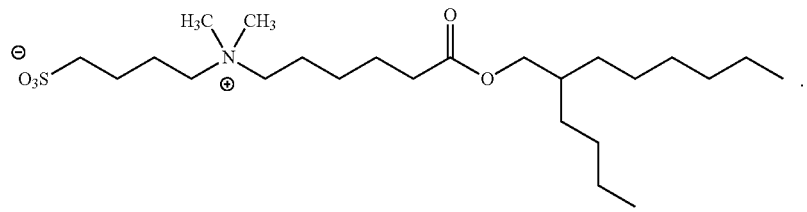

A fifth specific compound provided by the present disclosure is 2-butyloctyl 6-(dimethylamino)hexanoate N-oxide, having the following formula:

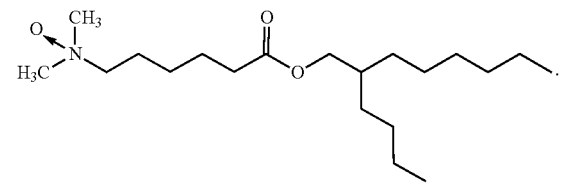

In the structure above, the notation "N→O" is intended to convey a non-ionic bonding interaction between nitrogen and oxygen.

A sixth specific compound provided by the present disclosure is 6-((2-butyloctyl)oxy)-6-oxohexan-1-aminium chloride, having the following formula:

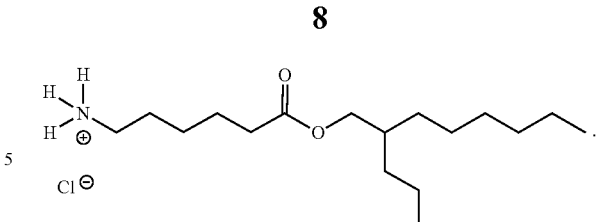

III. Synthesis.

The present surfactant compounds may be synthesized by various methods. One such method includes opening a lactam, which may be an N-alkylated lactam, to yield an amino acid having an N-terminus and a C-terminus. The C-terminus may then react with an alcohol under acidic conditions to provide an amino acid ester. The N-terminus of the amino acid may react with an alkylating agent to yield a quaternary amine salt, or the N-terminus of the amino acid ester may react with an acid to yield a quaternary amine salt.

Alternatively, the method may include opening a lactam to yield an amino acid having an N-terminus and a C-terminus. The N-terminus may then react with an alkylating agent to yield a tertiary amine. The C-terminus may then react with an alcohol under acidic conditions to provide an amino acid ester. The N-terminus of the amino acid may react with an alkylating agent to yield a quaternary amine salt, or the N-terminus of the amino acid ester may react with an acid to yield a quaternary amine salt.

The amino acid may be naturally occurring or synthetic or may be derived from a ring opening reaction of a lactam, such as propiolactam, butyrolactam, valerolactam, and caprolactam, for example. The ring-opening reaction may be either an acid or alkali catalyzed reaction, and an example of an acid catalyzed reaction is shown below in Scheme 1 in connection with caprolactam.

SCHEME 1

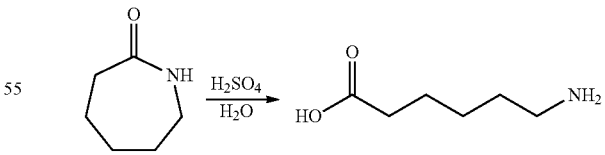

The amino acid may have as few as 2 or as many as 5 carbons between the N- and C-termini. The alkyl chain may be branched or straight. The alkyl chain may be interrupted with nitrogen, oxygen, or sulfur. The alkyl chain may be further substituted with one or more substituents selected from the group consisting of hydroxyl, amino, amido, sulfonyl, sulfonate, carboxyl, and carboxylate. The N-terminal nitrogen may be acylated or alkylated with one or more alkyl groups. For example, the amino acid may be 6-(dimethylamino)hexanoic acid.

The amino acid may be further elaborated as shown below in Scheme 2, wherein R, R', and R" may be hydrogen or $C_1$-$C_6$ alkyl, $R^2$ may be $C_5$-$C_{12}$ alkyl, and $R^3$ may be $C_3$-$C_{10}$ alkyl. For example, the amino acid may undergo an esterification reaction in which the amino acid is treated with an alcohol under acidic conditions to provide an amino acid ester.

SCHEME 2

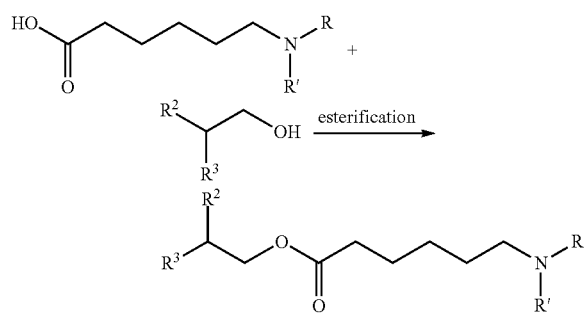

The resultant amino acid ester may then be alkylated or protonated to give an ammonium salt, as shown below in Scheme 3. Alkylation may be accomplished by treatment with an alkylating agent, such as methyl iodide, in the presence of a base, such as sodium carbonate, to provide a quaternary amine salt, the counterion of which is determined by the alkylating agent used. For example, treatment with methyl iodide provides the iodide salt of the quaternary ammonium species. Protonation may be accomplished by treating the amino acid ester with an acid, such as hydrochloric acid. The identity of the acid determines the counterion present in the salt. For example, treatment with hydrochloric acid results in the chloride salt of the ammonium species.

SCHEME 3

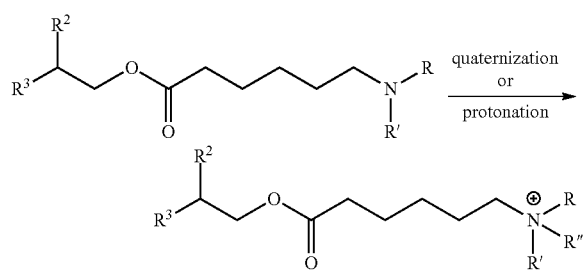

IV. Surfactant properties.

The compounds of the present disclosure demonstrate surface-active properties. These properties may be measured and described by various methods. One method by which surfactants may be described is by the molecule's critical micelle concentration (CMC). CMC may be defined as the concentration of a surfactant at which micelles form, and above which all additional surfactant is incorporated into micelles.

As surfactant concentration increases, surface tension decreases. Once the surface is completely overlaid with surfactant molecules, micelles begin to form. This point represents the CMC, as well as the minimum surface tension. Further addition of surfactant will not further affect the surface tension. CMC may therefore be measured by observing the change in surface tension as a function of surfactant concentration. One such method for measuring this value is the Wilhemy plate method. A Wilhelmy plate is usually a thin iridium-platinum plate attached to a balance by a wire and placed perpendicularly to the air-liquid interface. The balance is used to measure the force exerted on the plate by wetting. This value is then used to calculate the surface tension ($\gamma$) according to Equation 1:

$$\gamma = F/I \cos \theta \qquad \text{Equation 1:}$$

wherein I is equal to the wetted perimeter (2w+2d, in which w and d are the plate thickness and width, respectively) and $\cos \theta$, the contact angle between the liquid and the plate, is assumed to be 0 in the absence of an extant literature value.

Another parameter used to assess the performance of surfactants is dynamic surface tension. The dynamic surface tension is the value of the surface tension for a particular surface or interface age. In the case of liquids with added surfactants, this can differ from the equilibrium value. Immediately after a surface is produced, the surface tension is equal to that of the pure liquid. As described above, surfactants reduce surface tension; therefore, the surface tension drops until an equilibrium value is reached. The time required for equilibrium to be reached depends on the diffusion rate and the adsorption rate of the surfactant.

One method by which dynamic surface tension is measured relies upon a bubble pressure tensiometer. This device measures the maximum internal pressure of a gas bubble that is formed in a liquid by means of a capillary. The measured value corresponds to the surface tension at a certain surface age, the time from the start of the bubble formation to the occurrence of the pressure maximum. The dependence of surface tension on surface age can be measured by varying the speed at which bubbles are produced.

Surface-active compounds may also be assessed by their wetting ability on solid substrates as measured by the contact angle. When a liquid droplet comes in contact with a solid surface in a third medium, such as air, a three-phase line forms among the liquid, the gas and the solid. The angle between the surface tension unit vector, acting at the three-phase line and tangent at the liquid droplet, and the surface is described as the contact angle. The contact angle (also known as wetting angle) is a measure of the wettability of a solid by a liquid. In the case of complete wetting, the liquid is completely spread over the solid and the contact angle is 0°. Wetting properties are typically measured for a given compound at the concentration of 1-10× CMC, however, it is not a property that is concentration-dependent therefore measurements of wetting properties can be measured at concentrations that are higher or lower.

In one method, an optical contact angle goniometer may be used to measure the contact angle. This device uses a digital camera and software to extract the contact angle by analyzing the contour shape of a sessile droplet of liquid on a surface.

Potential applications for the surface-active compounds of the present disclosure include formulations for use as shampoos, hair conditioners, detergents, spot-free rinsing solutions, floor and carpet cleaners, cleaning agents for graffiti removal, wetting agents for crop protection, adjuvants for crop protection, and wetting agents for aerosol spray coatings.

It will be understood by one skilled in the art that small differences between compounds may lead to substantially different surfactant properties, such that different compounds may be used with different substrates, in different applications. For example, small changes in the hydrophobic portion of the surfactant, such as a difference in the number of carbons in an alkyl chain, the presence of a branched alkyl chain, the number of branches in a branched alkyl chain, and the number of carbons in each branch of a branched alkyl chain, may lead to different surfactant properties. Likewise, in the case of cationic and anionic surfactants, different counterions may substantively change the surfactant properties of a compound.

The compounds are effective as surface-active agents, useful for wetting or foaming agents, dispersants, emulsifiers, and detergents, among other applications.

The amount of the compounds disclosed herein used in a formulation may be as low as about 0.001 wt. %, about 0.05 wt. %, about 0.1 wt. %, about 0.5 wt. %, about 1 wt. %, about 2 wt. %, or about 5 wt. %, or as high as about 8 wt. %, about 10 wt. %, about 15 wt. %, about 20 wt. %, or about 25 wt. %, or within any range defined between any two of the foregoing values.

The following non-limiting Examples are provided to demonstrate the different properties of the different surfactants.

EXAMPLES

Nuclear magnetic resonance (NMR) spectroscopy was performed on a Bruker 500 MHz spectrometer. The critical micelle concentration (CMC) was determined by the Wilhelmy plate method at 23° C. with a tensiometer (DCAT 11, DataPhysics Instruments GmbH) equipped with a Pt—Ir plate. Dynamic surface tension was determined with a bubble pressure tensiometer (Krüss BP100, Krüss GmbH), at 23° C. Contact angle was determined with the optical contact angle goniometer (OCA 15 Pro, DataPhysics GmbH) equipped with a digital camera.

Example 1a

Synthesis of 6-((2-butyloctypoxy)-N,N,N-trimethyl-6-oxohexan-1-aminium iodide

2-Butyloctyl 6-(dimethylamino)hexanoate (2.04 mmol, 700 mg) was dissolved in acetonitrile (10 mL). Sodium carbonate (2.44 mmol, 259 mg) was added, and the mixture was stirred at room temperature for 10 minutes. Methyl iodide (6.12 mmol, 0.38 mL) was added, and the mixture was heated to 40° C. for 24 hours before cooling to room temperature. The mixture was filtered and the solvent was removed under vacuum to give 6-((2-butyloctyl)oxy)-N,N,N-trimethyl-6-oxohexan-1-aminium iodide as a yellow solid in 90% yield. $^1$H NMR (500 MHz, DMSO) δ 3.93 (d, J=5.7 Hz, 2H), 3.29-3.22 (m, 2H), 3.04 (s, 9H), 2.34 (t, J=7.4 Hz, 2H), 1.73-1.53 (m, 5H), 1.33-1.25 (m, 18H), 0.88-0.85 (m, 6H).

Example 1b

Determination of Critical Micelle Concentration (CMC)

The critical micelle concentration (CMC) of the 6-((2-butyloctyl)oxy)-N,N,N-trimethyl-6-oxohexan-1-aminium iodide from Example 1a was tested. From the plot of the results show in FIG. 1, a CMC value could not be clearly determined at concentrations as high as 10 mg/mL, with the surface tension asymptotically approaching a value of about 27 mN/m. FIG. 1 is a plot of these results, showing surface tension versus concentration. From the plot of the results, the surface tension at the CMC is equal to or less than about 27 mN/m.

Example 2a

Synthesis of 6-((2-butyloctyl)oxy)-N,N-dimethyl-6-oxohexan-1-aminium 4-methylbenzenesulfonate 6-(Dimethylamino)hexanoic acid was treated with 2-butyloctan-1-ol and p-toluenesulfonic acid in benzene for 12 hours at 120° C. 6-((2-Butyloctyl)oxy)-N,N-dimethyl-6-oxohexan-1-aminium 4-methylbenzenesulfonate was isolated as a white waxy solid and recrystallized from acetone in 49% yield. $^1$H NMR (500 MHz, DMSO) δ 7.48 (dd, J=8.4, 0.6 Hz, 2H), 7.12 (dd, J=8.4, 0.6 Hz, 1H), 3.93 (d, J=5.7 Hz, 2H), 3.02-3.00 (m, 2H), 2.76 (d, J=5.0 Hz, 6H), 2.37-2.25 (m, 6H), 1.59-1.53 (m, 5H), 1.25-1.29 (m, 18H), 0.87 (td, J=6.8, 2.7 Hz, 6H).

Example 2b

Determination of Critical Micelle Concentration (CMC)

Figure 2A:
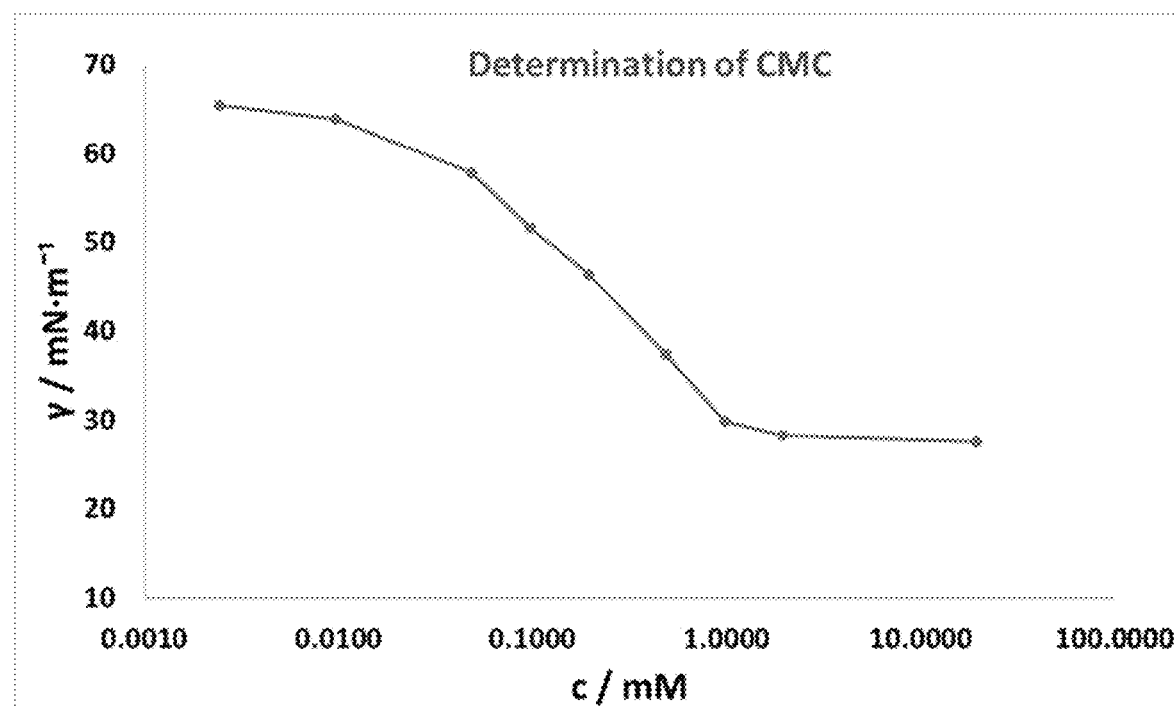
FIG. 2A shows a plot of surface tension versus concentration measured at pH=7 as described in Example 2B, wherein the Y axis depicts the surface tension (γ) in millinewtons per meter (mN/m) and the X axis depicts the concentration (c) in millimoles (mM).

The critical micelle concentration (CMC) of the 6-((2-butyloctyl)oxy)-N,N-dimethyl-6-oxohexan-1-aminium 4-methylbenzenesulfonate from Example 2a was tested. From the change in surface tension with concentration in water, the CMC was determined to be about 0.97 mmol. The plateau value of minimum surface tension that can be reached by this surfactant is about 27 mN/m, namely 27 mN/m±3 mN/m. FIG. 2A is a plot of these results, showing surface tension versus concentration. From the plot of the results, the surface tension at the CMC is equal to or less than about 30 mN/m.

Example 2c

Determination of Dynamic Surface Tension

Figure 2B:
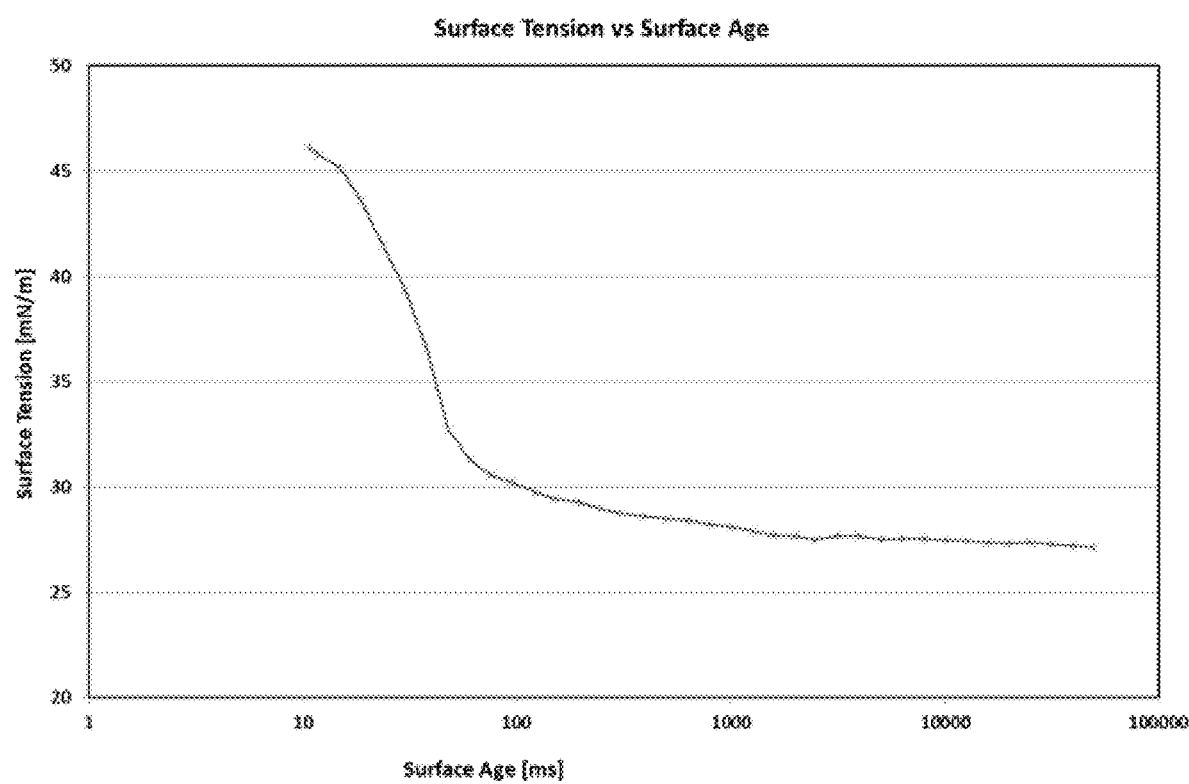
FIG. 2B shows a plot of dynamic surface tension as change in surface tension versus time as described in Example 2C, wherein the Y axis depicts the surface tension in millinewtons per meter (mN/m) and the X axis depicts the surface age in milliseconds (ms).

The dynamic surface tension of the 6-((2-butyloctyl)oxy)-N,N-dimethyl-6-oxohexan-1-aminium 4-methylbenzenesulfonate from Example 2a was determined with a bubble pressure tensiometer which measures the change of surface tension of a freshly created air-water interface with time. FIG. 2B presents a plot of the surface tension versus time, showing that surface tension in the time interval between 10 and 100 ms drops rapidly from about 46 mN/m to about 30 mN/m. In the time interval from 100 to 8,000 ms, the surface tension drops slowly from 30 mN/m to about 27 mN/m, approaching asymptotically the saturation value of the surface tension at the CMC.

Example 2d

Determination of Wetting Properties

In addition to surface tension and surface dynamics, the wetting properties of the 6-((2-butyloctyl)oxy)-N,N-dimethyl-6-oxohexan-1-aminium 4-methylbenzenesulfonate from Example 2a were tested on various surfaces. For example, hydrophobic substrates such as polyethylene-HD exhibit surface wetting with a contact angle of 24.3°. On oleophobic and hydrophobic substrates such as Teflon, the measured contact angle was much less than that of water's contact angle of 119°, at 48.2° (Table 1).

TABLE 1

| Substrate | CA of Surfactant (°) | Concentration | CA of water (°) |
|---|---|---|---|
| Teflon | 48.2 | 10x CMC | 119 |
| Polyethylene-HD | 24.3 | 10x CMC | 93.6 |
| Nylon | 13.5 | 10x CMC | 50 |
| Polyethylene terephthalate | 7.7 | 10x CMC | 65.3 |

Example 3a

Synthesis of 6-((2-butyloctyl)oxy)-N,N-dimethyl-6-oxohexan-1-aminium chloride

2-Butyloctyl 6-(dimethylamino)hexanoatewas treated with one equivalent of hydrochloric acid to provide 6-((2-butyloctyl)oxy)-N,N-dimethyl-6-oxohexan-1-aminium chloride.

Example 3b

Determination of Critical Micelle Concentration (CMC)

Figure 3:
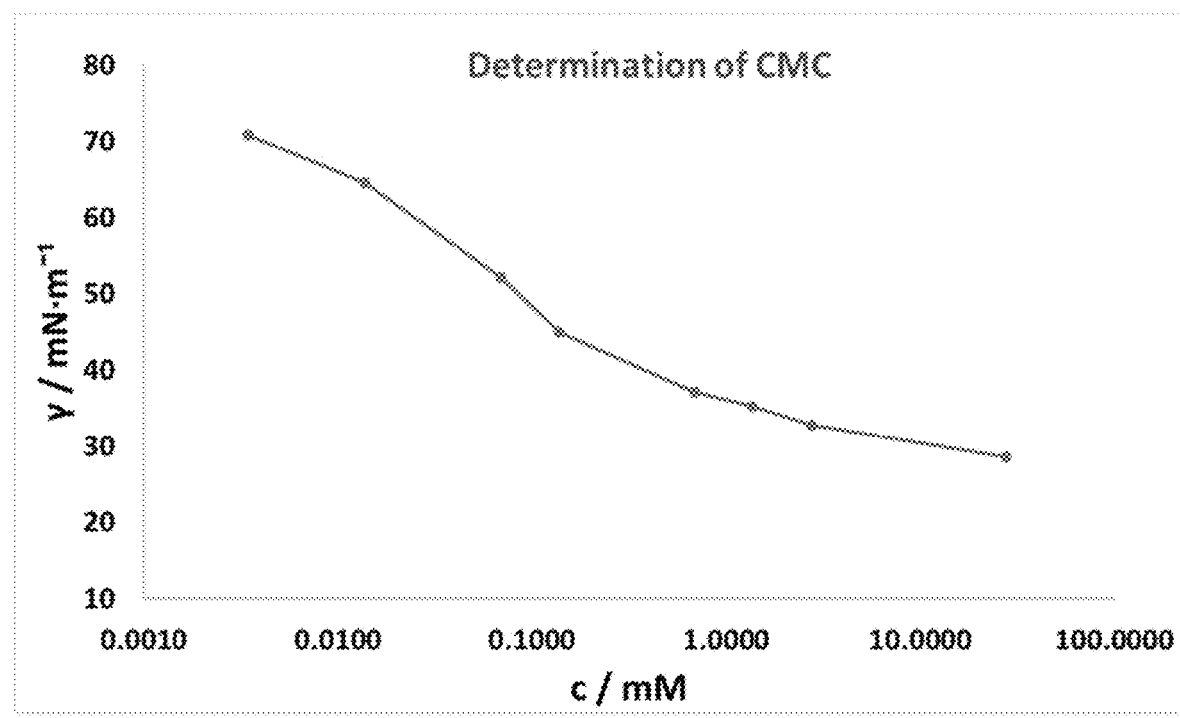
FIG. 3 shows a plot of surface tension versus concentration measured at pH=7 as described in Example 3B, wherein the Y axis depicts the surface tension (y) in millinewtons per meter (mN/m) and the X axis depicts the concentration (c) in millimoles (mM).

The critical micelle concentration (CMC) of the 6-((2-butyloctyl)oxy)-N,N-dimethyl-6-oxohexan-1-aminium chloride from Example 3a was tested. From the change in surface tension with concentration in water, the CMC was determined to be about 27.47 mmol. The minimum surface tension that can be reached by this surfactant is about 29 mN/m, namely 29 mN/m±3 mN/m. FIG. 3 is a plot of these results, showing surface tension versus concentration. From the plot of the results a CMC value could not be clearly determined at concentrations as high as 27.4 mmol, with the surface tension asymptotically approaching a value of about 29 mN/m.

Example 4a

Synthesis of 4-((6-((2-butyloctyl)oxy)-6-oxohexyl) dimethylammonio)butane-1-sulfonate 2-Butyloctyl 6-(dimethylamino)hexanoate (2.04 mmol, 700 mg) was dissolved in ethyl acetate (30 mL). 1,4-Butane sultone (3.06 mmol, 0.31 mL) was added. The mixture was heated to reflux for 12 hours, followed by evaporation of the solvent. The resultant white waxy solid was washed with acetone to give 4-((6-((2-butyloctyl)oxy)-6-oxohexyl)dimethylammonio)butane-1-sulfonate in 89% yield. $^1$H NMR (500 MHz, DMSO) δ3.93 (d, J=5.7 Hz, 2H), 3.30-3.28 (m, 4H), 2.97 (s, 3H), 2.49-2.43 (m, 2H), 2.34 (t, J=7.4 Hz, 2H), 1.96-1.76 (m, 9H), 1.27-1.25 (m, 18H), 0.88-0.85 (m, 6H).

Example 4b

Determination of Critical Micelle Concentration (CMC)

Figure 4A:
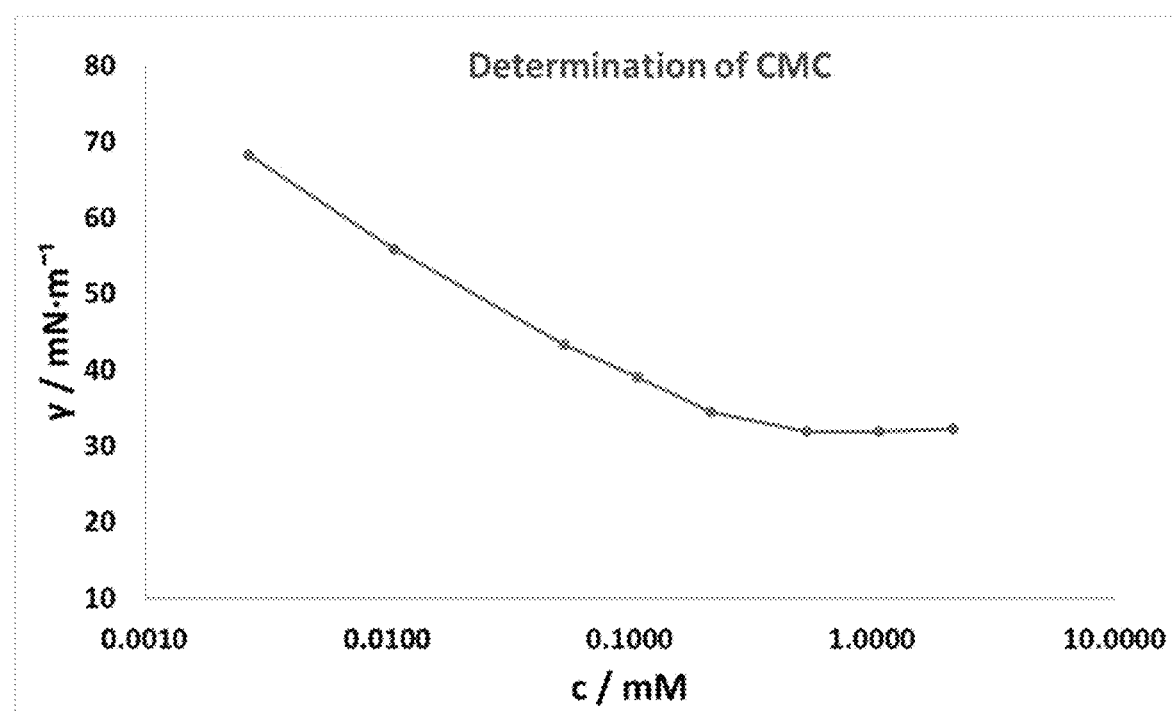
FIG. 4A shows a plot of surface tension versus concentration measured at pH=7 as described in Example 4B, wherein the Y axis depicts the surface tension (y) in millinewtons per meter (mN/m) and the X axis depicts the concentration (c) in millimoles (mM).

The critical micelle concentration (CMC) of the 4-((6-((2-butyloctyl)oxy)-6-oxohexyl)dimethylammonio)butane-1-sulfonate from Example 4a was tested. From the change in surface tension with concentration in water, the CMC was determined to be about 0.54 mmol. The plateau value of minimum surface tension that can be reached by this surfactant is about 32 mN/m, namely 32 mN/m±3 mN/m. FIG. 4A is a plot of these results, showing surface tension versus concentration. From the plot of the results, the surface tension at the CMC is equal to or less than about 32 mN/m.

Example 4c

Determination of Dynamic Surface Tension

Figure 4B:
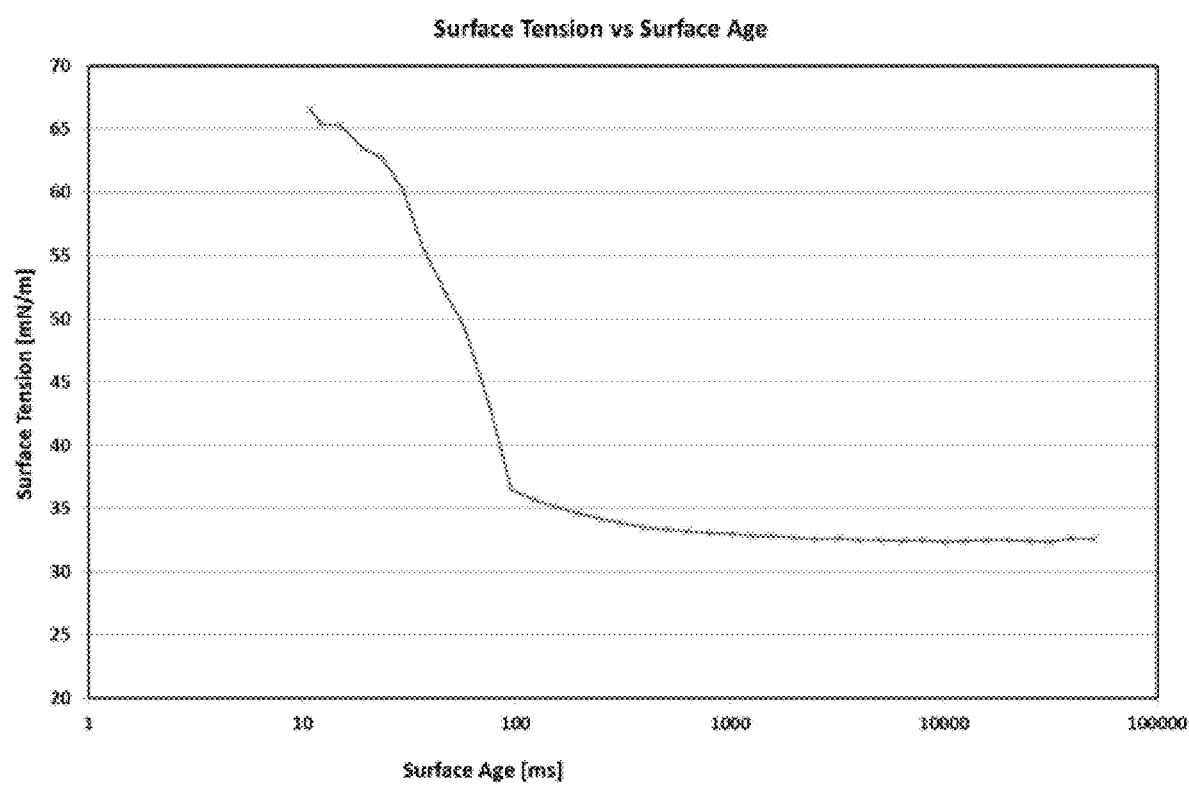
FIG. 4B shows a plot of dynamic surface tension as change in surface tension versus time as described in Example 4C, wherein the Y axis depicts the surface tension in millinewtons per meter (mN/m) and the X axis depicts the surface age in milliseconds (ms).

The dynamic surface tension of the 4-((6-((2-butyloctyl) oxy)-6-oxohexyl)dimethylammonio)butane-1-sulfonate from Example 4a was determined with a bubble pressure tensiometer which measures the change of surface tension of a freshly created air-water interface with time. FIG. 4B presents a plot of the surface tension versus time, showing that surface tension in the time interval between 10 and 100 ms drops rapidly from about 66 mN/m to about 36 mN/m. In the time interval from 100 to 8,000 ms, the surface tension drops slowly from 36 mN/m to about 32 mN/m, approaching asymptotically the saturation value of the surface tension at the CMC.

Example 4d

Determination of Wetting Properties

In addition to surface tension and surface dynamics, the wetting properties of the of the 4-((6-((2-butyloctyl)oxy)-6-oxohexyl)dimethylammonio)butane-1-sulfonate from Example 4a were tested on various surfaces. For example, hydrophobic substrates such as polyethylene-HD exhibit surface wetting with a contact angle of 44.4°. On oleophobic and hydrophobic substrates such as Teflon, the measured contact angle was much less than that of water's contact angle of 119°, at 62.2° (Table 2).

TABLE 2

| Substrate | CA of Surfactant (°) | Concentration | CA of water (°) |
|---|---|---|---|
| Teflon | 62.2 | 10x CMC | 119 |
| Polyethylene-HD | 44.4 | 10x CMC | 93.6 |
| Nylon | 28.7 | 10x CMC | 50 |
| Polyethylene terephthalate | 29.8 | 10x CMC | 65.3 |

Example 5a

Synthesis of 2-butyloctyl 6-(dimethylamino)hexanoate N-oxide

2-Butyloctyl 6-(dimethylamino)hexanoate was treated with hydrogen peroxide in water for 24 hours at 70° C. to give 2-butyloctyl 6-(dimethylamino)hexanoate N-oxide as an oil in 90% yield. $^1$H NMR (500 MHz, DMSO) δ 3.93 (d, J=5.7 Hz, 2H), 3.30-3.28 (m, 4H), 2.97 (s, 3H), 2.49-2.43

(m, 2H), 2.34 (t, J=7.4 Hz, 2H), 1.96-1.76 (m, 9H), 1.27-1.25 (m, 18H), 0.88-0.85 (m, 6H).

Example 5b

Determination of Critical Micelle Concentration (CMC)

Figure 5A:
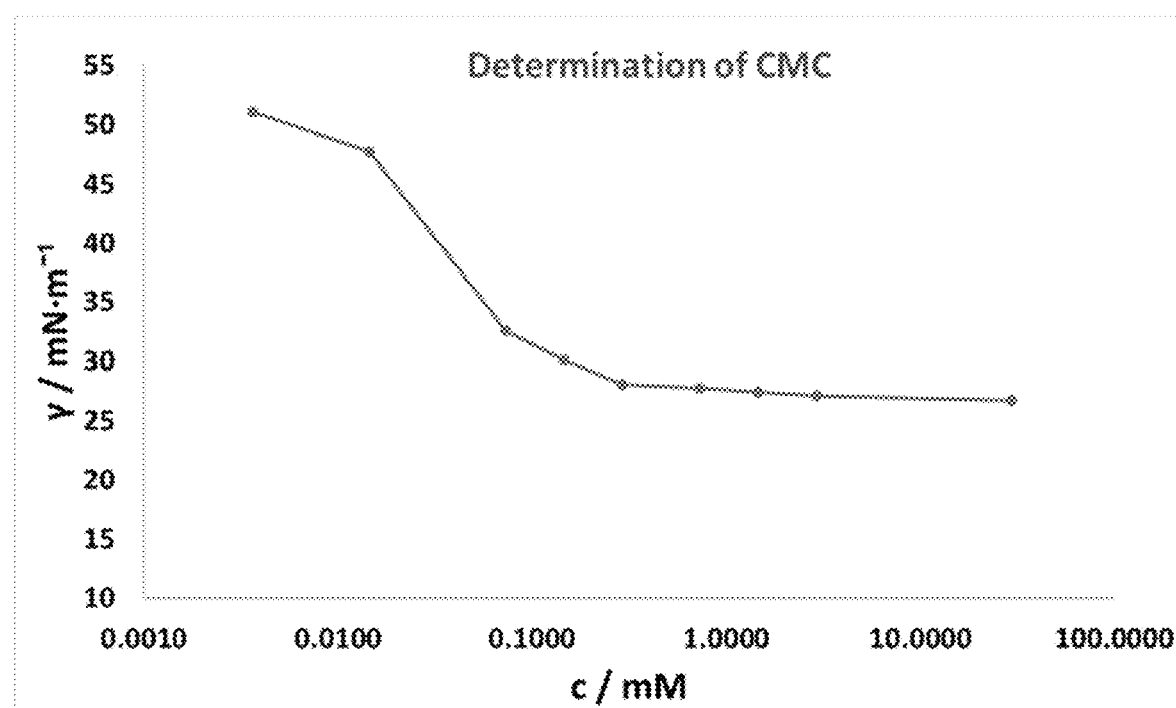
FIG. 5A shows a plot of surface tension versus concentration measured at pH=7 as described in Example 5B, wherein the Y axis depicts the surface tension (y) in millinewtons per meter (mN/m) and the X axis depicts the concentration (c) in millimoles (mM).

The critical micelle concentration (CMC) of the 2-butyloctyl 6-(dimethylamino)hexanoate N-oxide from Example 5a was tested. From the change in surface tension with concentration in water, the CMC was determined to be about 0.29 mmol. The plateau value of minimum surface tension that can be reached by this surfactant is about 28 mN/m, namely 28 mN/m±3 mN/m. FIG. 5A is a plot of these results, showing surface tension versus concentration. From the plot of the results, the surface tension at the CMC is equal to or less than about 28 mN/m.

Example 5c

Determination of Dynamic Surface Tension

Figure 5B:
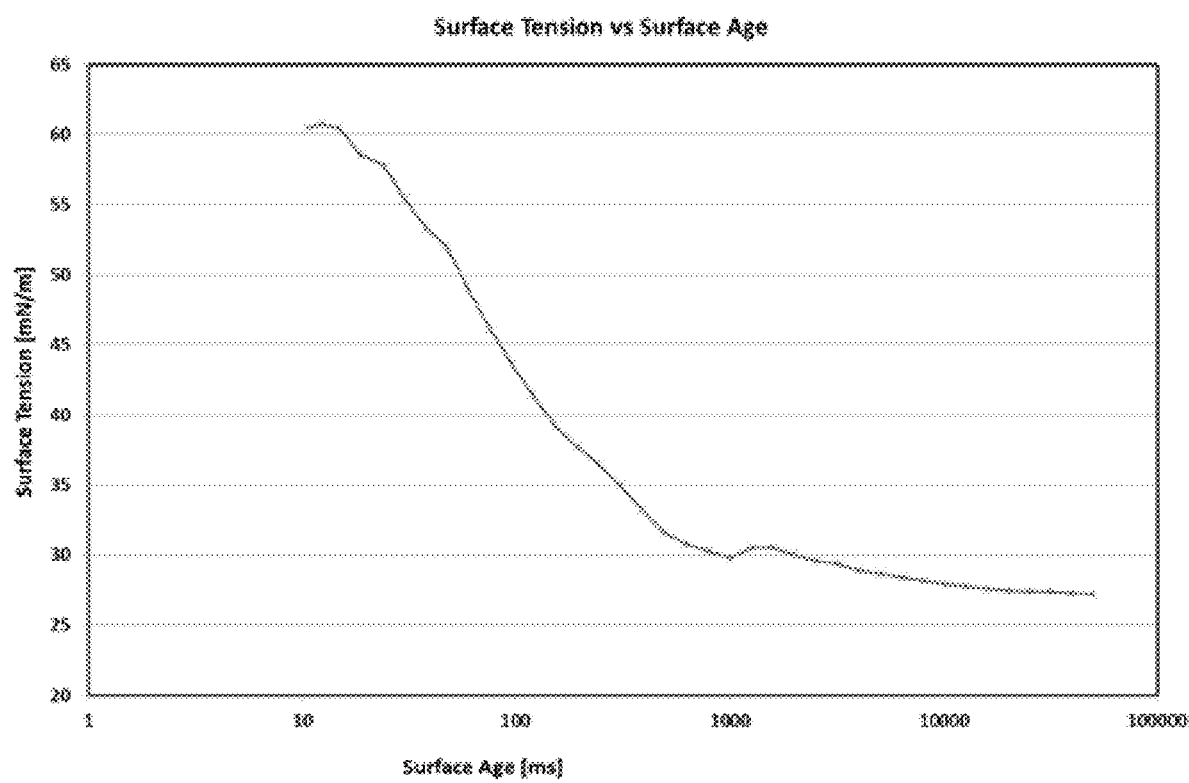
FIG. 5B shows a plot of dynamic surface tension as change in surface tension versus time as described in Example 5C, wherein the Y axis depicts the surface tension in millinewtons per meter (mN/m) and the X axis depicts the surface age in milliseconds (ms).

The dynamic surface tension of the 2-butyloctyl 6-(dimethylamino)hexanoate N-oxide from Example 5a was determined with a bubble pressure tensiometer which measures the change of surface tension of a freshly created air-water interface with time. FIG. 5B presents a plot of the surface tension versus time, showing that surface tension in the time interval between 10 and 1,000 ms drops rapidly from about 60 mN/m to about 30 mN/m. In the time interval from 1,000 to 8,000 ms, the surface tension drops slowly from 30 mN/m to about 28 mN/m, approaching asymptotically the saturation value of the surface tension at the CMC.

Example 5d

Determination of Wetting Properties

In addition to surface tension and surface dynamics, the wetting properties of the of the 2-butyloctyl 6-(dimethylamino)hexanoate N-oxide from Example 5a were tested on various surfaces. For example, hydrophobic substrates such as polyethylene-HD exhibit surface wetting with a contact angle of 31.6°. On oleophobic and hydrophobic substrates such as Teflon, the measured contact angle was much less than that of water's contact angle of 119°, at 41.5° (Table 3).

TABLE 3

| Substrate | CA of Surfactant (°) | Concentration | CA of water (°) |
|---|---|---|---|
| Teflon | 41.0 | 10x CMC | 119 |
| Polyethylene-HD | 31.9 | 10x CMC | 93.6 |
| Nylon | 38.5 | 10x CMC | 50 |
| Polyethylene terephthalate | 9.2 | 10x CMC | 65.3 |

Example 6a

Synthesis of 6-((2-butyloctyl)oxy)-6-oxohexan-1-aminium chloride

2-Butyloctyl 6-(dimethylamino)hexanoate was treated with 1 equivalent of hydrochloric acid.

Example 6b

Determination of Critical Micelle Concentration (CMC)

Figure 6A:
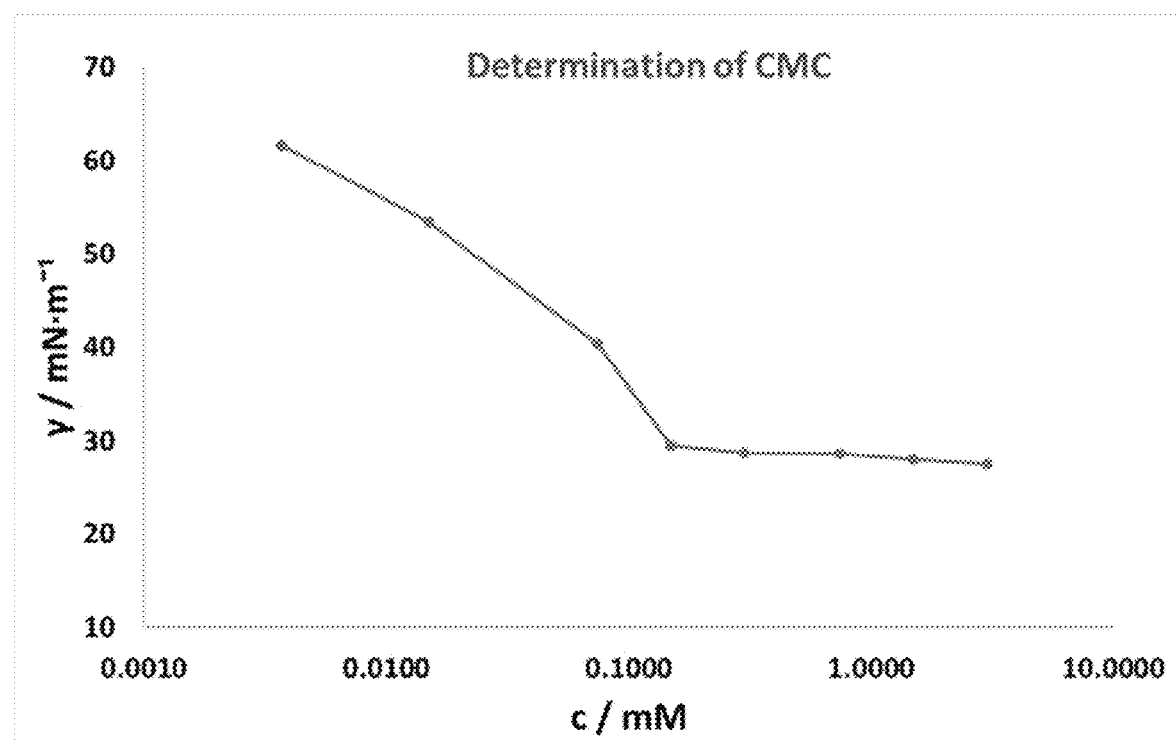
FIG. 6A shows a plot of surface tension versus concentration measured at pH=7 as described in Example 6B, wherein the Y axis depicts the surface tension (y) in millinewtons per meter (mN/m) and the X axis depicts the concentration (c) in millimoles (mM).

The critical micelle concentration (CMC) of the 6-((2-butyloctyl)oxy)-6-oxohexan-1-aminium chloride from Example 6a was tested. From the change in surface tension with concentration in water, the CMC was determined to be about 0.15 mmol. The plateau value of minimum surface tension that can be reached by this surfactant is about 27 mN/m, namely 27 mN/m±3 mN/m. FIG. 6A is a plot of these results, showing surface tension versus concentration. From the plot of the results, the surface tension at the CMC is equal to or less than about 30 mN/m.

Example 6c

Determination of Dynamic Surface Tension

Figure 6B:
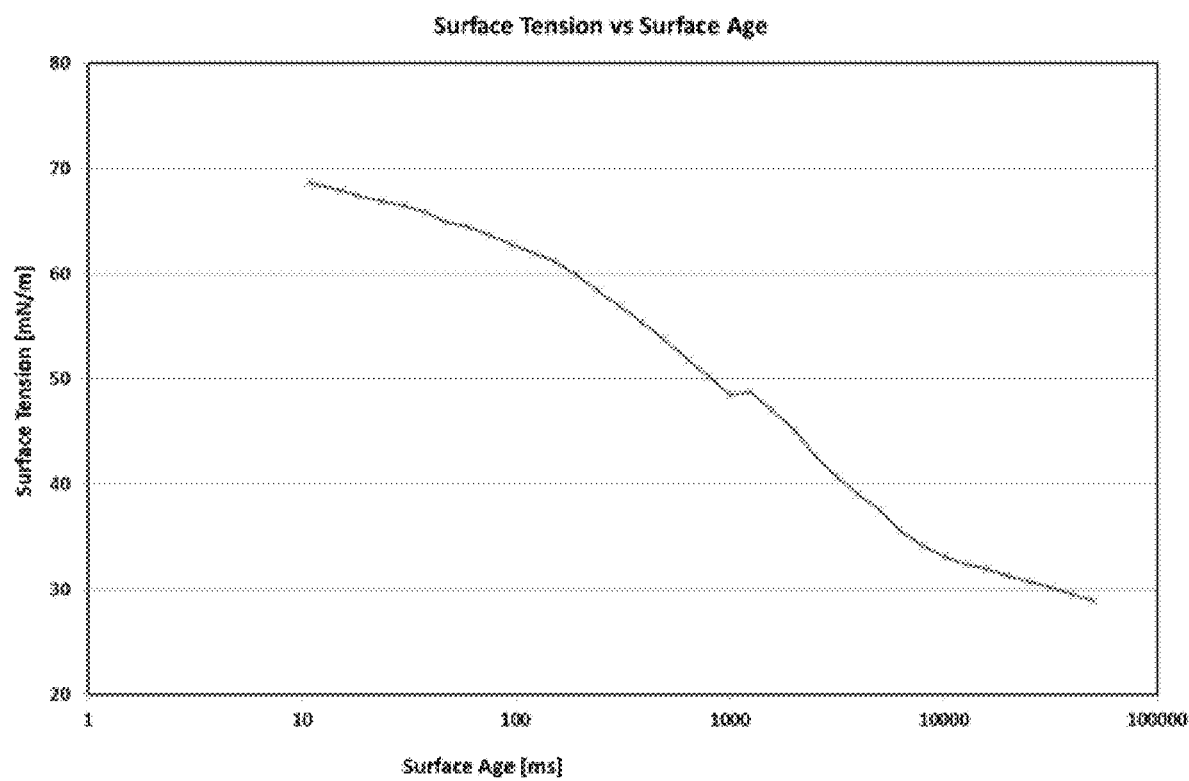
FIG. 6B shows a plot of dynamic surface tension as change in surface tension versus time as described in Example 6C, wherein the Y axis depicts the surface tension in millinewtons per meter (mN/m) and the X axis depicts the surface age in milliseconds (ms).

The dynamic surface tension of the 6-((2-butyloctyl)oxy)-6-oxohexan-1-aminium chloride from Example 6a was determined with a bubble pressure tensiometer which measures the change of surface tension of a freshly created air-water interface with time. FIG. 6B presents a plot of the surface tension versus time, showing that surface tension in the time interval between 10 and 8,000 ms drops slowly from about 69 mN/m to about 29 mN/m, with a slight plateau of about 49 mN/m at a surface age of 1,000 ms, approaching the saturation value of the surface tension at the CMC.

Example 6d

Determination of Wetting Properties

In addition to surface tension and surface dynamics, the wetting properties of the of the 6-((2-butyloctyl)oxy)-6-oxohexan-1-aminium chloride from Example 6a were tested on various surfaces. For example, hydrophobic substrates such as polyethylene-HD exhibit surface wetting with a contact angle of 25.8°. On oleophobic and hydrophobic substrates such as Teflon, the measured contact angle was much less than that of water's contact angle of 119°, at 48.7° (Table 4).

TABLE 4

| Substrate | CA of Surfactant (°) | Concentration | CA of water (°) |
|---|---|---|---|
| Teflon | 48.7 | 10x CMC | 119 |
| Polyethylene-HD | 25.8 | 10x CMC | 93.6 |
| Nylon | 24.5 | 10x CMC | 50 |
| Polyethylene terephthalate | 20.1 | 10x CMC | 65.3 |

Aspects

Aspect 1 is a compound of the following formula:

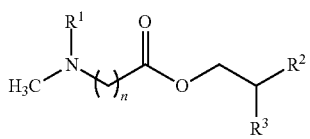

wherein $R^1$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); $R^2$ is $C_5$-$C_{12}$ alkyl; $R^3$ is $C_3$-$C_{10}$ alkyl; the terminal nitrogen is optionally further substituted with $R^4$, wherein $R^4$ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide, iodide, and 4-methylbenzenesulfonate.

Aspect 2 is the compound of Aspect 1, wherein the compound is 6-((2-butyloctyl)oxy)-N,N,N-trimethyl-6-oxohexan-1-aminium iodide, having the following formula:

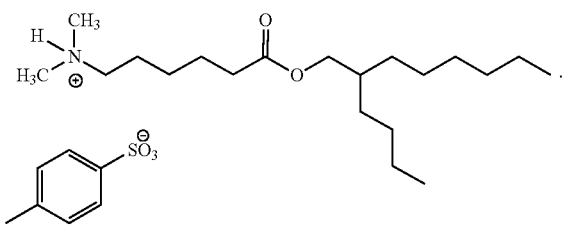

Aspect 3 is the compound of Aspect 2, having a critical micelle concentration (CMC) of about 21.30 mmol in water.

Aspect 4 is the compound of Aspect 1, wherein the compound is 6-((2-butyloctyl)oxy)-N,N-dimethyl-6-oxohexan-1-aminium 4-methylbenzenesulfonate, having the following formula:

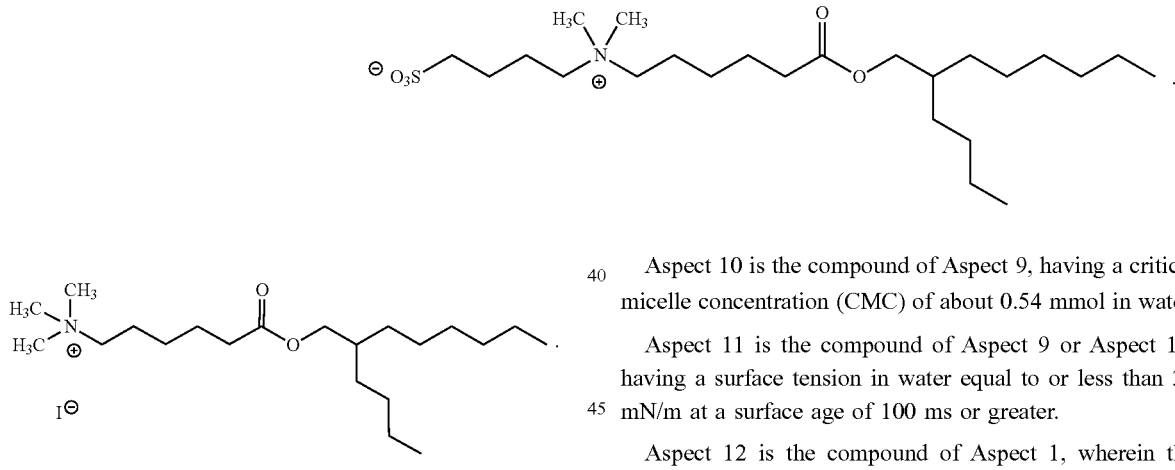

Aspect 5 is the compound of Aspect 4, having a critical micelle concentration (CMC) of about 0.97 mmol in water.

Aspect 6 is the compound of either Aspect 4 or Aspect 5, having a surface tension in water equal to or less than 30 mN/m at a surface age of 100 ms or greater.

Aspect 7 is the compound of Aspect 1, wherein the compound is 6-((2-butyloctyl)oxy)-N,N-dimethyl-6-oxohexan-1-aminium chloride, having the following formula:

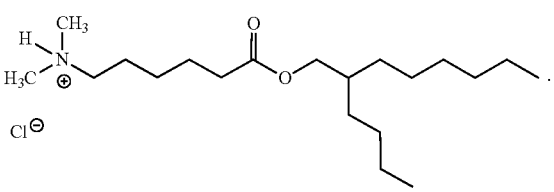 [SMILES: [Cl-] ; CCCCCCC(CCCC)COC(=O)CCCCC[NH+](C)C]

Aspect 8 is the compound of Aspect 7, having a critical micelle concentration (CMC) of about 27.47 mmol in water.

Aspect 9 is the compound of Aspect 1, wherein the compound is 4-((6-((2-butyloctyl)oxy)-6-oxohexyl)dimethylammonio)butane-1-sulfonate, having the following formula:

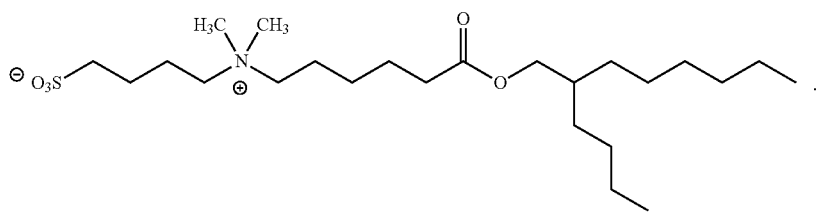

Aspect 10 is the compound of Aspect 9, having a critical micelle concentration (CMC) of about 0.54 mmol in water.

Aspect 11 is the compound of Aspect 9 or Aspect 10, having a surface tension in water equal to or less than 36 mN/m at a surface age of 100 ms or greater.

Aspect 12 is the compound of Aspect 1, wherein the compound is 2-butyloctyl 6-(dimethylamino)hexanoate N-oxide, having the following formula:

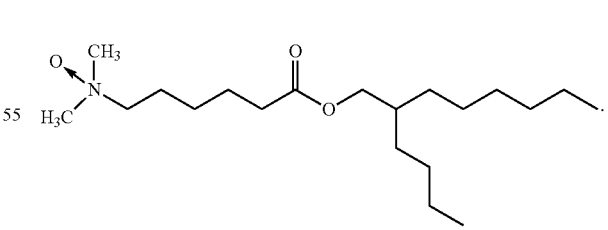

Aspect 13 is the compound of Aspect 12, having a critical micelle concentration (CMC) of about 0.29 mmol in water.

Aspect 14 is the compound of Aspect 12 or Aspect 13, having a surface tension in water equal to or less than 30 mN/m at a surface age of 1,000 ms or greater.

Aspect 15 is a compound of the following formula:

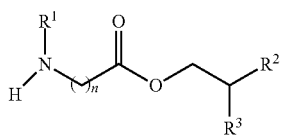

wherein R¹ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); R² is $C_5$-$C_{12}$ alkyl; R³ is $C_3$-$C_{10}$ alkyl; the terminal nitrogen is optionally further substituted with R⁴, wherein R⁴ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide and iodide.

Aspect 16 is the compound of Aspect 15, wherein the compound is 6-((2-butyloctyl)oxy)-6-oxohexan-1-aminium chloride, having the following formula:

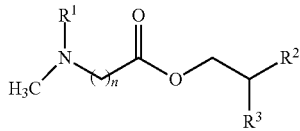

Aspect 17 is the compound of Aspect 16, having a critical micelle concentration (CMC) of about 0.15 mmol in water.

Aspect 18 is the compound of Aspect 16 or Aspect 17, having a surface tension in water equal to or less than 49 mN/m at a surface age of 1,000 ms or greater.

Aspect 19 is a liquid composition comprising: a medium; and a surfactant of the following formula:

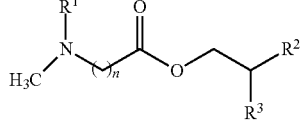

wherein R¹ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); R² is $C_5$-$C_{12}$ alkyl; R³ is $C_3$-$C_{10}$ alkyl; the terminal nitrogen is optionally further substituted with R⁴, wherein R⁴ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide, iodide, and 4-methylbenzenesulfonate.

Aspect 20 is the composition of Aspect 19, wherein the medium is water.

Aspect 21 is a liquid composition comprising: a medium; and a surfactant of the following formula:

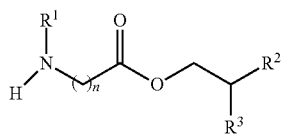

wherein R¹ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; n is an integer from 2 to 5 (including 2 and 5); R² is $C_5$-$C_{12}$ alkyl; R³ is $C_3$-$C_{10}$ alkyl; the terminal nitrogen is optionally further substituted with R⁴, wherein R⁴ is chosen from hydrogen, an oxygen atom, and $C_1$-$C_6$ alkyl, wherein the $C_1$-$C_6$ alkyl may be substituted with carboxylates, hydroxyls, sulfonyls, or sulfonates; and an optional counterion may be associated with the compound and, if present, the counterion may be selected from the group consisting of chloride, bromide and iodide.

Aspect 22 is the composition of Aspect 21, wherein the medium is water.

The invention claimed is:
1. A compound of the following formula:

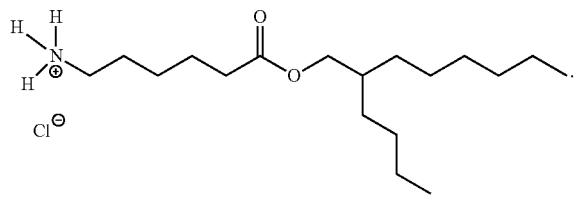

wherein R¹ is selected from the group consisting of hydrogen, an oxygen atom, and a substituted or unsubstituted $C_1$-$C_6$ alkyl, wherein the $C_1$-$C_6$ alkyl comprises a group selected from the group consisting of carboxylates, hydroxyls, sulfonyls, or sulfonates;
n is an integer from 2 to 5;
R² is $C_5$ or $C_6$ alkyl;
R³ is $C_3$ or $C_4$ alkyl;
the terminal nitrogen is optionally further substituted with R⁴, wherein R⁴ chosen from hydrogen, an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;
and if R⁴ is present then the compound comprises a counterion selected from the group consisting of chloride, bromide, iodide, and 4-methylbenzenesulfonate.

2. The compound of claim 1, wherein the compound is 6-((2-butyloctyl)oxy)-N,N,N-trimethyl-6-oxohexan-1-aminium iodide, having the following formula:

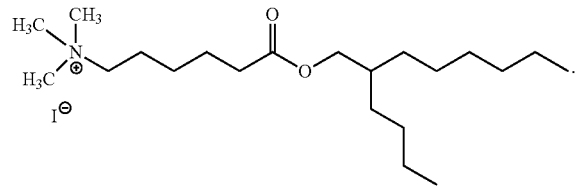 [SMILES: CCCCCCC(CCCC)COC(=O)CCCCC[N+](C)(C)C ; [I-]]

3. The compound of claim 2, having a critical micelle concentration (CMC) of about 21.30 mmol in water.

4. The compound of claim 1, wherein the compound is 6-((2-butyloctyl)oxy)-N,N-dimethyl-6-oxohexan-1-aminium 4-methylbenzenesulfonate, having the following formula:

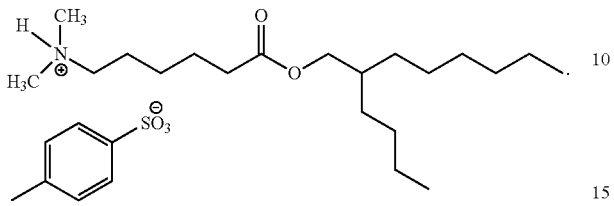

5. The compound of claim 4, having a critical micelle concentration (CMC) of about 0.97 mmol in water.

6. The compound of claim 4, having a surface tension in water equal to or less than 30 mN/m at a surface age of 100 ms or greater.

7. The compound of claim 1, wherein the compound is 6-((2-butyl octyl)oxy)-N,N-dim ethyl-6-oxohexan-1-aminium chloride, having the following formula:

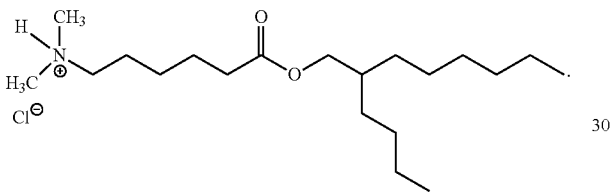

8. The compound of claim 7, having a critical micelle concentration (CMC) of about 27.47 mmol in water.

9. The compound of claim 1, wherein the compound is 4-((6-((2-butyloctyl)oxy)-6-oxohexyl)dimethylammonio) butane-1-sulfonate, having the following formula:

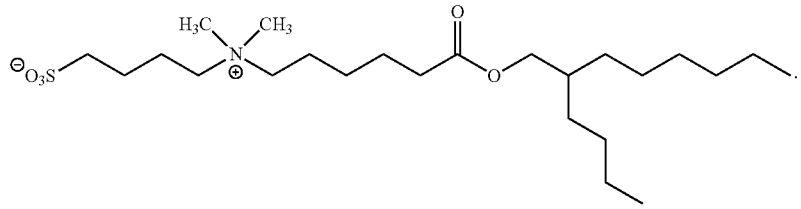

10. The compound of claim 9, having a critical micelle concentration (CMC) of about 0.54 mmol in water.

11. The compound of claim 9, having a surface tension in water equal to or less than 36 mN/m at a surface age of 100 ms or greater.

12. The compound of claim 1, wherein the compound is 2-butyloctyl 6-(dimethylamino)hexanoate N-oxide, having the following formula:

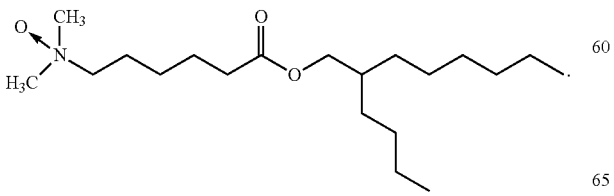

13. The compound of claim 12, having a critical micelle concentration (CMC) of about 0.29 mmol in water.

14. The compound of claim 12, having a surface tension in water equal to or less than 30 mN/m at a surface age of 1,000 ms or greater.

15. A compound of the following formula:

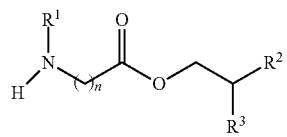

wherein 1e is selected from the group consisting of an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;

n is an integer from 2 to 5;

$R^2$ is $C_5$-$C_{12}$ alkyl;

$R^3$ is $C_3$-$C_{10}$ alkyl;

the terminal nitrogen is optionally further substituted with $R^4$, wherein $R^4$ chosen from an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;

and if $R^4$ is present then the compound comprises a counterion selected from the group consisting of chloride, bromide and iodide.

16. A liquid composition comprising:
a medium; and
a surfactant of the following formula:

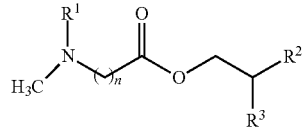

wherein $R^1$ is selected from the group consisting of hydrogen, an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;

n is an integer from 2 to 5;

$R^2$ is $C_5$ or $C_6$ alkyl;

$R^3$ is $C_3$ or $C_4$ alkyl;

the terminal nitrogen is optionally further substituted with $R^4$, wherein $R^4$ chosen from hydrogen, an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;

and if $R^4$ is present then the compound comprises a counterion selected from the group consisting of chloride, bromide, iodide, and 4-methylbenzenesulfonate.

17. The composition of claim 16, wherein the medium is water.

18. A liquid composition comprising:
a medium; and
a surfactant of the following formula:

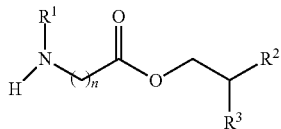

wherein le is selected from the group consisting of an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;

n is an integer from 2 to 5;

$R^2$ is $C_5$ or $C_6$ alkyl;

$R^3$ is $C_3$ or $C_4$ alkyl;

the terminal nitrogen is optionally further substituted with $R^4$, wherein $R^4$ chosen from an oxygen atom, and a substituted or unsubstituted $C_1$-$C_6$ alkyl, wherein the substituted $C_1$-$C_6$ alkyl comprises a group selected from the group consisting of carboxylates, hydroxyls, sulfonyls, or sulfonates;

and if $R^4$ is present then the compound comprises a counterion selected from the group consisting of chloride, bromide and iodide.

19. The composition of claim 18, wherein the medium is water.

* * * * *